United States Patent [19]

Norman

[11] Patent Number: 4,603,574
[45] Date of Patent: Aug. 5, 1986

[54] BLOOD PRESSURE TRANSDUCER TESTER
[75] Inventor: Jacob J. Norman, Westminster, Calif.
[73] Assignee: American Hospital Supply Corporation, Evanston, Ill.
[21] Appl. No.: 692,976
[22] Filed: Jan. 22, 1985
[51] Int. Cl.⁴ ............................................. G01C 25/00
[52] U.S. Cl. ....................................................... 73/4 R
[58] Field of Search ............... 73/1 R, 4 R, 1 B, 720, 73/721, 726, 727; 200/42 R, 42 T, 42 A, 43; 128/672, 673, 674, 675

[56]   References Cited
U.S. PATENT DOCUMENTS

| | | | |
|---|---|---|---|
| 2,964,733 | 12/1960 | Raju | 200/43 |
| 3,063,283 | 11/1962 | Polansky | 73/1 R |
| 3,311,187 | 3/1967 | Haggard, Jr. | 200/42 R |
| 4,499,903 | 2/1985 | Furst et al. | 73/4 R |

Primary Examiner—Jerry W. Myracle
Attorney, Agent, or Firm—Weissenberger & Peterson

[57] ABSTRACT

Calibration testing of a blood pressure transducer can be performed in immediate proximity to the body of the patient by including in either the transducer housing or the housing of a connector located adjacent thereto, a pair of membrane switches on opposite sides of the housing. The switches are connected in series with each other and with a shunting resistor which, when connected across one input and one output port of the transducer's circuit, will produce a predetermined pressure reading. The switches are so arranged as to require simultaneous actuation from two sides of the housing to prevent accidental actuation of the testing circuit by the patient.

11 Claims, 4 Drawing Figures

BLOOD PRESSURE TRANSDUCER TESTER

This invention relates to a pressure signal tester for a blood pressure transducer, and more specifically a tester including an actuator which can be located in immediate proximity to the patient.

BACKGROUND OF THE INVENTION

Blood pressure transducers are commonly used in hospitals to display or record a continuing indication of the patient's blood pressure. In typical applications, the transducer is taped to the patient's arm and connected to a vein through a cannula with a stopcock. A cable about one foot in length extends from the transducer to a connector which is also affixed to the patient's arm. In a preferred type of apparatus, the connector contains compensating circuitry for the calibration and temperature-tracking of the transducer, and provides for the universal interconnection of the transducer assembly to various types of monitors.

In a typical hospital environment, the blood pressure monitor is mounted on a shelf or other location at least several feet away from the patient and often not readily accessible by the nursing staff while attending the patient. One of the duties of the nurse is to check from time to time whether the transducer system is functioning, particularly after the patient has been moved or the transducer system has been manipulated.

A null check of the transducer can readily be accomplished by closing the stopcock and venting the transducer to atmosphere. A pressure check is ordinarily accomplished by pressing a test button on the monitor which shunts one of the arms of the transducer's strain gauge bridge with a known resistance such that, if the transducer circuitry is functioning properly, the monitor should show a steady predetermined pressure reading.

It has long been felt desirable to give the nursing staff the ability to make the pressure check while attending the patient and without going to the monitor. However, it has previously been considered impractical to do so because the patient was likely to accidentally depress the pressure check button and thereby to disable the monitoring equipment.

SUMMARY OF THE INVENTION

The invention allows the pressure check to be performed at the patient site by mounting, in either the connector or the transducer housing itself, a pair of switches located on opposite sides of the connector or transducer housing. These switches may be of the membrane type and may be inconspicuous so as not to attract the patient's attention. Inasmuch as both of them need to be depressed simultaneously to make a pressure check, the patient cannot accidentally disable the monitor by pushing the transducer or connector against an object.

DESCRIPTION OF THE PREFERRED EMBODIMENT

Figure 1:
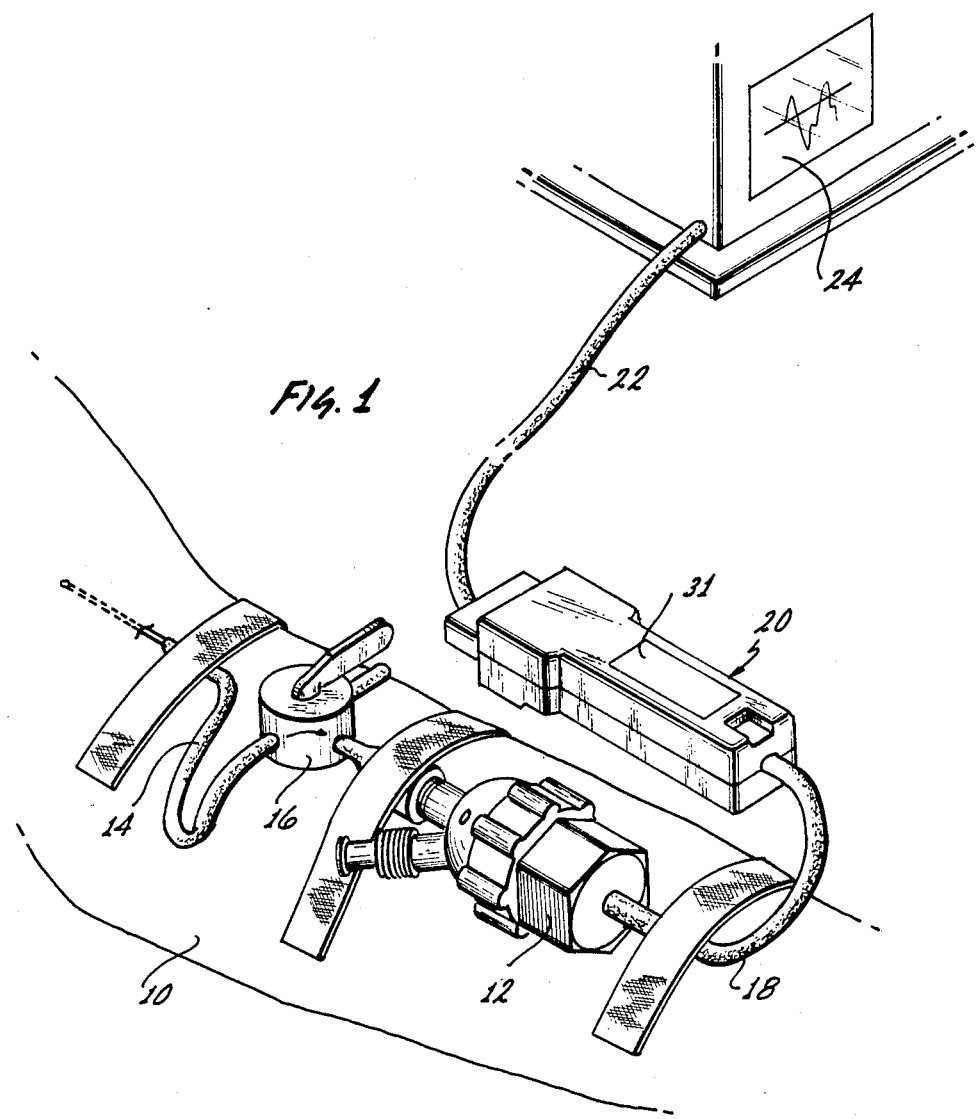
FIG. 1 is a perspective view illustrating the relative positions of the patient, transducer, connector and monitor in a typical environment.

In FIG. 1, 10 denotes the limb of a patient. A transducer assembly consisting of transducer 12, cable 18, and connector 20 is affixed to the limb 10 in an appropriate manner. The transducer 12 is connected to a vein of the patient by means of a cannula 14 provided with a stop-cock 16. The transducer 12 is connected by a short linking cable 18 to a connector 20 which contains conventional compensating circuits for the transducer 12. A long connecting cable 22 typically links the connector 20 to the monitor 24.

Figure 2A:
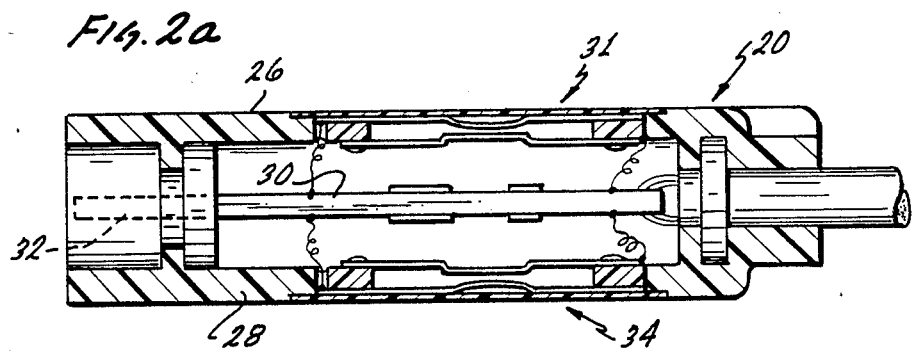
FIG. 2a is a certical longitudinal section through the connector showing a preferred location for membrane switches of this invention.

Turning now to FIG. 2a, it will be seen that the connector 20 is of generally elongated construction and includes a housing having outer walls 26, 28 between which a conventional circuit board 30 and a connector plate 32 are secured. In accordance with the invention, a pressure tester including a pair of low-profile switches such as membrane switches 31, 34 of the type commonly found in computer control panels is provided in the connector 20. The switches 31, 34 are preferably low-profile so that they can be unobtrusively embedded in the outer walls 26, 28 and are so located as to require a symmetrical (i.e. simultaneous) actuation in order to perform a test. In the preferred embodiments, the membrane switches 31, 34 face in opposite directions so that they can be operated simultaneously (thereby actuating the pressure tester) only by squeezing them between the thumb and index finger.

Figure 2B:
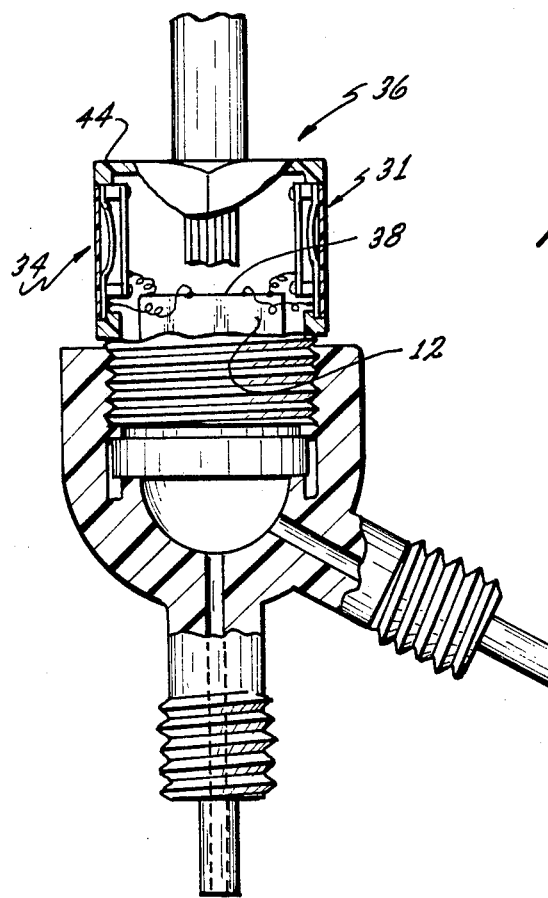
FIG. 2b is a vertical section through the transducer showing an alternate location of the membrane switches.

FIG. 2b shows an alternative mounting of the membrane switches. In that figure the transducer housing is generally shown at 36 with the conventional strain gauge and its circuitry being schematically shown at 38. In this embodiment the membrane switches 31, 34 are embedded in opposite sides of the housing wall 44 of transducer 36. Because even minor handling may temporarily affect the readings of the very sensitive transducer 36, the embodiment of FIG. 2b is less desirable than that of FIG. 2a; however, its use may be indicated in instances where the entire transducer circuitry is contained within the transducer housing and no separate connector is used.

Figure 3:
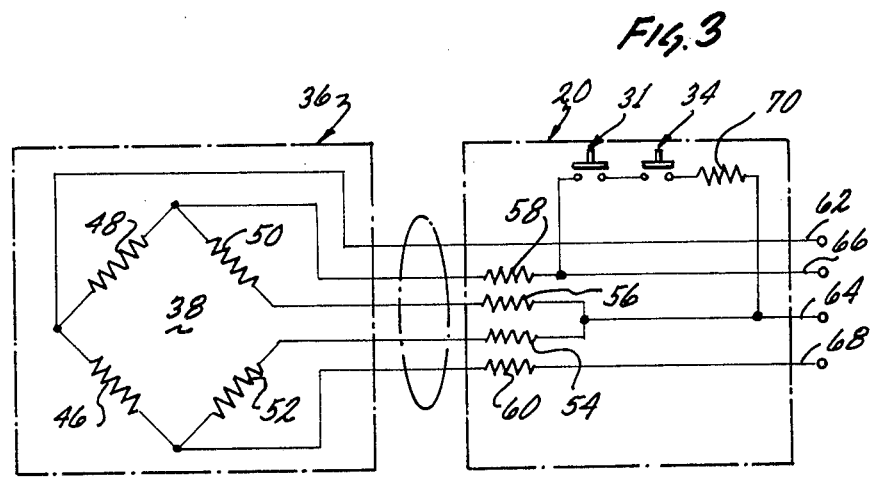
FIG. 3 is a circuit diagram of a typical transducer involved in this invention.

FIG. 3 shows a typical circuit of the embodiment of FIG. 2a, it being understood that this circuitry would be essentially the same or similar for the embodiment of FIG. 2b. In FIG. 3, the transducer 36 contains a conventional Wheatstone bridge circuit whose resistive arms 46, 48, 50 and 52 are the legs of the pressure-responsive strain gauge 38. The bridge circuit is open at one end and is connected by five leads to the connector 20 which contains a balancing resistor 54 for producing zero output at zero pressure, a temperature compensating resistor 56 for causing the transducer to track evenly at different temperatures, and a pair of identical dropping resistors 58, 60 for calibrating the pressure signal output of the transducer 36. The leads 62, 64 are the output ports of the bridge, and the leads 66, 68 are its input ports.

In accordance with the invention, the arm 50 of the bridge is selectively shunted by a test resistor 70 so dimensioned as to cause the transducer 36 to produce a known pressure signal, e.g. 5.0 mV representing a pressure reading of 100 mmHg when excited with 10.0 Vdc power. The shunt is actuated by the simultaneous depression of the membrane switches 31, 34. If either of these switches is depressed alone, the shunt does not occur and the transducer functions in the normal manner.

It will be understood that the invention is not limited to a Wheatstone bridge circuit, but is equally applicable to other types of sensor circuits such as half bridges or shear stress gauges. In all of these, current input and output ports are provided, and a test resistor can be selectively shunted by a pair of series-connected switches across one input and one output port in the same manner as described above.

I claim:

1. A blood pressure transducer system, comprising:
    (a) a transducer assembly adapted to be attached to a patient and including a transducer having a housing;
    (b) electrical testing means for causing said transducer assembly to put out a simulated pressure signal corresponding to a predetermined blood pressure level; and
    (c) actuating means located in said transducer for selectively actuating said testing means, said actuating means including a pair of series-connected switches located on opposite sides of said housing.

2. A blood pressure transducer system, comprising:
    (a) a transducer assembly adapted to be attached to a patient and including a connector having a housing;
    (b) electrical testing means for causing said transducer assembly to put out a simulated pressure signal corresponding to a predetermined blood pressure level; and
    (c) actuating means located in said transducer for selectively actuating said testing means, said actuating means including a pair of series-connected switches located on opposite sides of said housing.

3. A blood pressure transducer system, comprising:
    (a) a transducer assembly adapted to be attached to a patient;
    (b) electrical testing means for causing said transducer assembly to put out a simulated pressure signal corresponding to a predetermined blood pressure level; and
    (c) actuating means located in said assembly for selectively actuating said testing means, said actuating means including a pair of switches connected in series.

4. The system of claim 3, in which said switches are low profile switches.

5. The system of claim 4, in which said switches are membrane switches.

6. The system of claim 3, in which said switches are so positioned on said assembly as to require a symmetrical movement to simultaneously actuate them.

7. The system of claim 6, in which said transducer assembly includes a sensor circuit having input and output ports, and said testing means include a test resistor selectively shuntable across one input and one output port so as to produce a predetermined output signal from said transducer assembly.

8. The system of claim 7, in which said test resistor is connected in series with said series-connected switches, said series-connected resistor and switches being connected across said input and output ports.

9. The system of claim 6, in which said transducer assembly includes a Wheatstone bridge circuit, and said testing means include a test resistor selectively shuntable across one leg of said bridge circuit to produce a predetermined output signal from said transducer assembly.

10. The system of claim 9, in which said test resistor is connected in series with said series-connected switches, said resistor and switches being connected in parallel with said leg of said bridge circuit.

11. The system of claim 3, in which said switches are so positioned on opposite sides of said assembly as to require a squeezing movement from both sides to simultaneously actuate them.

* * * * *